(12) United States Patent
Friese et al.

(10) Patent No.: US 10,014,078 B2
(45) Date of Patent: Jul. 3, 2018

(54) METHOD AND SYSTEM FOR PRESENTING MEDICAL CONTENTS

(71) Applicant: SIEMENS AKTIENGESELLSCHAFT, Munich (DE)

(72) Inventors: Thomas Friese, Munich (DE); Vladyslav Ukis, Nuremberg (DE)

(73) Assignee: Siemens Aktiengesellschaft, Munich (DE)

( * ) Notice: Subject to any disclaimer, the term of this patent is extended or adjusted under 35 U.S.C. 154(b) by 420 days.

(21) Appl. No.: 14/150,950

(22) Filed: Jan. 9, 2014

(65) Prior Publication Data

US 2014/0236628 A1 Aug. 21, 2014

(30) Foreign Application Priority Data

Feb. 21, 2013 (DE) .................. 10 2013 202 825

(51) Int. Cl.
G06Q 50/00 (2012.01)
G16H 30/20 (2018.01)
G16H 10/60 (2018.01)
G06F 19/00 (2018.01)

(52) U.S. Cl.
CPC ........... *G16H 30/20* (2018.01); *G06F 19/322* (2013.01); *G16H 10/60* (2018.01)

(58) Field of Classification Search
CPC ............................. G16H 30/20; G16H 10/60
See application file for complete search history.

(56) References Cited

U.S. PATENT DOCUMENTS

| 8,694,646 B1 * | 4/2014 | Kothari | ............... H04L 63/0435 709/227 |
| 2005/0096619 A1 | 5/2005 | Ito | |
| 2006/0009692 A1 | 1/2006 | Fukuda et al. | |

(Continued)

FOREIGN PATENT DOCUMENTS

| CN | 1598874 A | 3/2005 |
| CN | 1704020 A | 12/2005 |
| CN | 102819760 A | 12/2012 |

OTHER PUBLICATIONS

First Office Action issued by the Chinese Patent Office for corresponding Chinese Application No. 2014100413447 dated Aug. 3, 2016.

*Primary Examiner* — Christopher L Gilligan
(74) *Attorney, Agent, or Firm* — Harness, Dickey & Pierce, P.L.C.

(57) ABSTRACT

A method is disclosed for presenting medical contents. An embodiment of the method includes generating a pseudonymized case study from a patient study using a case upload client in a hospital environment by providing the patient study with a marker and by removing personal patient data from the patient study; sending the pseudonymized case study to a computing center via the Internet and virtualizing the pseudonymized case study; transmitting the virtualized pseudonymized case study to the hospital environment via an Internet connection and mapping the virtualized pseudonymized case study with the personal patient data by way of a display client; and displaying the mapped medical contents by way of the display client with the viewer. A system, a case upload client and a case upload server for presenting medical contents, are also disclosed.

6 Claims, 2 Drawing Sheets

(56) References Cited

U.S. PATENT DOCUMENTS

| | | | |
|---|---|---|---|
| 2007/0103984 A1* | 5/2007 | Kavuri | G06F 3/0605 365/185.17 |
| 2007/0192139 A1* | 8/2007 | Cookson | G06F 19/322 705/3 |
| 2009/0103789 A1 | 4/2009 | Danner et al. | |
| 2011/0110568 A1* | 5/2011 | Vesper | G06F 19/321 382/128 |
| 2011/0191767 A1 | 8/2011 | Pinsky et al. | |
| 2013/0208966 A1* | 8/2013 | Zhao | G06F 9/5072 382/131 |
| 2013/0325805 A1* | 12/2013 | Tochilnik | G06F 21/6254 707/638 |

\* cited by examiner

FIG 2

METHOD AND SYSTEM FOR PRESENTING MEDICAL CONTENTS

PRIORITY STATEMENT

The present application hereby claims priority under 35 U.S.C. § 119 to German patent application number DE 102013202825.3 filed Feb. 21, 2013, the entire contents of which are hereby incorporated herein by reference.

FIELD

At least one embodiment of the present invention generally lies in the field of methods and systems for presenting medical contents.

BACKGROUND

Imaging methods are very important in medical diagnostics. In this case, image data produced by different modalities (nuclear spin, ultrasound, x-ray, etc.) are acquired using PACS (Picture Archiving and Communication System) or RIS (Radiology Information System). At the same time, medical imaging systems are increasingly being provided "in-house" in hospitals using a client-server architecture. Corresponding image viewers or "viewers" are therefore frequently changed at diagnostic workstations. The costs of adapting the diagnostic workstations to new software applications and the costs of maintaining them are high in this case.

SUMMARY

At least one embodiment of the invention is directed to a method and/or a system which can be used to present medical contents, in which case they are intended to be quickly ready for use and are intended to be cost-effective in terms of maintenance and upkeep.

Features, advantages or alternative embodiments mentioned in this case can likewise also be applied to the other claimed subject matters and vice versa. In other words, the objective claims (which are directed to a system, an apparatus or a product, for example) can also be developed using the features described or claimed in connection with the method and vice versa. The corresponding functional features of the method are formed in this case by way of corresponding objective modules, in particular hardware modules.

One aspect of at least one embodiment of the invention provides a method for presenting medical contents which has a display client in a hospital environment and a presentation client in a computing center, wherein the presentation client is set up to virtualize contents and the display client is set up to display contents virtualized by the presentation client by way of a viewer. The method comprises:

generating a pseudonymized case study from a patient study using a case upload client in the hospital environment by providing the patient study with a marker and by removing access-protected patient data from the patient study and by removing personal patient data from the patient study,
  sending the pseudonymized case study from the case upload client via a secure Internet protocol,
  receiving the pseudonymized case study via the secure Internet protocol using a case upload server in the computing center, wherein the case upload server is equipped with an interface to a medical server in the computing center in order to forward the pseudonymized case study to the medical server,
  retrieving the pseudonymized case study by way of the presentation client which is equipped with an interface to the medical server,
  virtualizing the pseudonymized case study by way of the presentation client,
  transmitting the virtualized pseudonymized case study via an Internet connection,
  mapping the virtualized pseudonymized case study with the personal patient data by way of the display client, and
  displaying the mapped medical contents by way of the display client with the viewer.

The above-described embodiments of the method according to the invention can also be in the form of a computer program product with a computer program, the computer being caused to carry out the above-described method according to the invention if the computer program is executed on the computer or on a processor of the computer.

One embodiment of the invention provides a system for presenting medical contents, which system has: a display client in a hospital environment and a presentation client in a computing center, wherein the presentation client is set up to virtualize contents and the display client is set up to display contents virtualized by the presentation client via a viewer. The system comprises:

a case upload client in the hospital environment, and
  a case upload server in the computing center, wherein the case upload client is set up to generate a pseudonymized case study from a patient study by providing the patient study with a marker and by removing personal patient data from the patient study, and wherein the case upload client is also set up to send the pseudonymized case study via a secure Internet protocol, and wherein the case upload server is set up to receive the pseudonymized case study via the secure Internet protocol and is equipped with an interface to a medical server in the computing center in order to forward the pseudonymized case study to the medical server, wherein the presentation client is equipped with an interface to the medical server in order to retrieve the pseudonymized case study from the medical server and to virtualize said case study, and wherein the display client is set up to map the pseudonymized case study, virtualized after transmission via an Internet connection, with the personal patient data and to display said case study on the viewer.

One embodiment of the invention provides a storage medium for storing a computer program which can be read in and/or loaded by a digital computer and comprises instructions which are used to carry out the steps as claimed in the preceding method claims if the instructions are executed on the digital computer.

An alternative embodiment provides a storage medium which is intended to store the above-described, computer-implemented method and can be read by a computer.

Within the scope of the invention, not all steps of the method necessarily have to be carried out on the same computer entity but rather they can also be carried out on different computer entities. The sequence of method steps can also be varied, if necessary.

BRIEF DESCRIPTION OF THE DRAWINGS

The following detailed description of the figures discusses example embodiments, which should not be understood in a restrictive manner, with their features and further advantages using the drawing, in which.

DETAILED DESCRIPTION OF THE EXAMPLE EMBODIMENTS

The present invention will be further described in detail in conjunction with the accompanying drawings and embodiments. It should be understood that the particular embodiments described herein are only used to illustrate the present invention but not to limit the present invention.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

Specific structural and functional details disclosed herein are merely representative for purposes of describing example embodiments of the present invention. This invention may, however, be embodied in many alternate forms and should not be construed as limited to only the embodiments set forth herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

One aspect of at least one embodiment of the invention provides a method for presenting medical contents which has a display client in a hospital environment and a presentation client in a computing center, wherein the presentation client is set up to virtualize contents and the display client is set up to display contents virtualized by the presentation client via a viewer. The method comprises:

generating a pseudonymized case study from a patient study using a case upload client in the hospital environment by providing the patient study with a marker and by removing access-protected patient data from the patient study and by removing personal patient data from the patient study, sending the pseudonymized case study from the case upload client via a secure Internet protocol, receiving the pseudonymized case study via the secure Internet protocol using a case upload server in the computing center, wherein the case upload server is equipped with an interface to a medical server in the computing center in order to forward the pseudonymized case study to the medical server, retrieving the pseudonymized case study via the presentation client which is equipped with an interface to the medical server, virtualizing the pseudonymized case study via the presentation client, transmitting the virtualized pseudonymized case study via an Internet connection, mapping the virtualized pseudonymized case study with the personal patient data via the display client, and displaying the mapped medical contents via the display client with the viewer.

"Method" denotes an operation which is carried out in a system having the components of the described type, with the result that medical contents are presented.

The term "medical contents" denotes medical data which can be presented or visualized and are in the form of images, values, diagrams, text or sound recordings, for example. The contents can be formatted differently. The contents can be stored in a distributed manner.

The expression "display client" denotes a computer entity or a computer in a hospital environment, which computer is connected to a screen. Software (or a computer program) which can be referred to as an image indicator or "viewer" is also implemented on the display client or is linked to the latter. Interaction between the display client, the screen and the viewer makes it possible to present or depict the medical contents on the screen or other output devices.

The expression "presentation client" denotes a computer entity or a computer which is suitable for virtualizing contents and transmitting the latter to the display client. In this case, transmission may be effected from the presentation client in the computing center to the display client in the hospital environment via an Internet connection.

"Virtualize" means the local execution of applications or simulation of computers without the applications having to be installed or the simulated computers having to be physically present.

The presentation client in the computing center may itself be virtualized. The presentation client may be virtualized by a medical server in the computing center by virtue of the medical server simulating the presentation client.

The term "computing center" denotes a region which is outside the hospital environment and in which computers and other electronic devices maintained by the provider of a computing service (hardware, software, storage space, platforms, services etc.) are situated.

The term "case upload client" denotes a computer which is situated in the hospital environment. The case upload client has an interface which can be used to receive medical content data. Image data which were produced by modalities can be received, for example. The data produced by modalities or by other electronic devices can be stored in different formats. For example, the data can be stored in a PACS archiving system (PACS—Picture Archiving and Communications System) and/or can be made available to an RIS information system (RIS—Radiology Information System). In order to make it possible to integrate the different components with one another and to embed PACS in hospital information systems, standards such as DICOM or HL7-based standards are additionally used and are likewise installed on the case upload client. In particular, the case upload client has a connection to a secure Internet connection or Internet connection which can be used to transmit data to other computers via the Internet in a secure manner.

The term "case upload server" denotes a computer which is situated in the computing center. The case upload server has an interface or a connection to the Internet in order to be able to receive secure data which were sent by the case upload client. The case upload client in the hospital environment and the case upload server in the computing center may therefore be those entities which establish a connection to or via the Internet.

The term "pseudonymized case study" denotes one or more files with medical contents which is based on a patient study. In this case, a patient study may be a complete patient file or part of the patient file and may have a multiplicity of medical contents of the type mentioned above (image, value, diagram etc.). However, in contrast to the patient study, the pseudonymized case study does not contain any personal patient data (also PHI data; Protected Health Information which needs to be protected from unauthorized access). Instead of personal patient data, the pseudonymized case study has a marker representing a key which can be used to regain or request the personal patient data. Successful requesting of the personal patient data presupposes the knowledge of which marker was allocated for a particular patient study. In particular, the knowledge or method for allocating the marker remains on computers or entities in the hospital environment. The knowledge for allocating the marker may therefore be unknown in the computing center. Personal patient data are therefore not transmitted via the Internet, in which case the term "personal patient data" is used to mean data which allow conclusions to be drawn on the person from the patient study without a relatively large amount of effort or prior knowledge. These could be the name, address, date of birth, place of birth or similar contents of this type. The deletion of the personal patient data from the patient study may denote an operation in which these relevant data are removed and are physically no longer present. In particular, no conclusions can therefore normally be drawn on the patient as a person from the pseudonymized case study. An exception in this case could only involve the remaining medical contents themselves, for instance x-rays, allowing conclusions to be indirectly drawn on the person. The marker may therefore also be interpreted as a pseudonym and is part of the pseudonymized study which also still has the purely medical contents. In particular, these are image data which are held or stored in the PACS or RIS system.

In other words, one aspect of the present application relates to the fact that the uploader client removes patient health information (PHI) from the header and pixel data before they are sent to the data center in pseudonymized form. The identity of the data is therefore concealed. The mapping between PHI data and pseudonyms remains on the user computer.

"Secure Internet protocol" may be used to mean the setting-up of a so-called "https:" connection.

The terms "send" and "receive" etc. may be understood in such a manner that a connection for interchanging data generally exists, is used or is set up between two computers. The type of connection may vary in this case. In particular, said terms are used to mean the connections via the Internet, WAN, WLAN or other types of network.

The term "interface" is used to mean a connection point of a computer, via which the computer can interchange data.

The term "medical server" may denote a central computer or a multiplicity of computers in a computing center on which applications (in the sense of software applications) provided by a provider of the computing service or the computing center are implemented. These may be particularly computation-intensive or maintenance-intensive applications.

The term "map" may denote an operation in which at least two contents which are or were initially separated are associated with one another again. In the method described here, the term "map" first of all requires detection of exactly which marker was assigned to which patient study when deleting the personal patient data. The mapping can therefore be based on an algorithm or a database which reveals a correct assignment. A simple database assignment can suffice if the marker of the pseudonymized patient study remains unchanged. If the marker is changed using an algorithm, the knowledge of this algorithm should be used in order to be able to assign the correct personal patient data. Furthermore, the mapping may describe an operation in which the personal patient data which have been cut out are inserted into the pseudonymized study again, with the result that a patient study is produced therefrom again. The "mapped" patient study may be suitable for being presented on a screen using a viewer. In this case, the mapped patient study may not be able to be distinguished from the original patient study for a user if no changes have been made to the medical contents presented.

An idea behind at least one embodiment of the invention involves producing a pseudonymized case study which is suitable for being transmitted via a secure Internet connection. This is required for reasons of data protection for the patient. This ultimately implements a method which makes it possible to present and process medical contents which are not present in situ in the hospital but rather are present in a computing center. In this case, storage resources, computing service resources and resources for maintaining the systems which make the system more favorable and more fail-safe than a hospital's own data center can be provided in the computing center. During presentation, the user in the hospital does not notice that the purely medical part of the patient study is physically present in the computing center. Presentation or processing of a patient study is preceded in this case by pseudonymized transmission of the medically relevant data to the computing center. A study is therefore set up by the viewer in two stages, the first part running outside in a computing center and the second part remaining with the personal patient data in the hospital. Final mapping produces the complete patient study required for use in the hospital.

According to another embodiment of the method, the mapping is based on the use of the same marker which is used when generating the pseudonymized case study.

The mapping may therefore be based on the fact that a simple database assignment suffices to assign the correct personal patient data to a pseudonymized case study using the marker.

According to another embodiment of the method, when the patient study is retrieved by a user in the hospital environment, the case upload client sends an identification feature to the case upload server, which identification feature is based on the marker with which the pseudonymized case study was provided.

The retrieval of the patient study by the user in the hospital may temporally precede the transmission of the pseudonymized case study. However, the retrieval may also be effected at a time at which the pseudonymized case study is already present in the computing center or on the medical server. If the patient study is called, the case upload client may then transmit an identification feature, which identifies the user in the hospital or the hospital itself, to the case upload server. Mapping can be accelerated with the allocation of identification features since this is used to signal which pseudonymized case study should be transferred to which hospital or which destination address. Furthermore, this makes it possible to prevent unauthorized third parties from being able to access the computing center or from accessing medical contents. In this case, retrieval may have a call instruction which is used to transmit the identification feature after the user in the hospital has made a corresponding input. The identification feature can additionally be used to conceal the origin of a pseudonymized case study. Both the medical contents and the users in the hospital are therefore rendered anonymous. In this case, the identification feature is likewise based on the original marker with which the pseudonymized case study was provided. It is therefore possible to determine which user would like to and can retrieve precisely which pseudonymized case study.

According to another embodiment of the method, the case upload server is equipped with an interface to a database and stores the identification feature in the database, and the presentation client is equipped with an interface to the database and requests the identification feature from the database.

The practice of setting up a database in the computing center may be helpful for allocating or managing access rights. The identification features stored in the database can be used to stipulate and modify who has access to a particular pseudonymized case study. The access rights can therefore be managed for a plurality of users in a hospital or on a hospital-wide basis. If different hospitals have access, this makes it possible to set up a secure access group for the pseudonymized case studies stored in the computing center.

According to another embodiment of the method, a diagnostic workstation is set up in the hospital environment, at which workstation the viewer is displayed and the mapped medical contents can be processed.

The diagnostic workstation in the hospital may be set up at different locations and may therefore be in the form of a distributed system and may have input devices such as a mouse, keyboard etc. When virtualizing the mapped patient study, it is possible for the user at the diagnostic workstation to process the medical contents. Imaging methods or applications may be provided in the computing center for this purpose. Although presentation takes place in a "remote" manner, that is to say over a large distance, via the Internet, processing can be accelerated in this manner since both the pseudonymized case study to be processed and the imaging methods and applications are held in the computing center.

The above-described embodiments of the method according to the invention can also be in the form of a computer program product with a computer program, the computer being caused to carry out the above-described method according to the invention if the computer program is executed on the computer or on a processor of the computer.

One embodiment of the invention provides a system for presenting medical contents, which system has: a display client in a hospital environment and a presentation client in a computing center, wherein the presentation client is set up to virtualize contents and the display client is set up to display contents virtualized by the presentation client by way of a viewer. The system comprises:
  a case upload client in the hospital environment, and
  a case upload server in the computing center, wherein the
    case upload client is set up to generate a pseudonymized case study from a patient study by providing the patient study with a marker and by removing personal patient data from the patient study, and wherein the case upload client is also set up to send the pseudonymized case study via a secure Internet protocol, and wherein the case upload server is set up to receive the pseudonymized case study via the secure Internet protocol and is equipped with an interface to a medical server in the computing center in order to forward the pseudonymized case study to the medical server, wherein the presentation client is equipped with an interface to the medical server in order to retrieve the pseudonymized case study from the medical server and to virtualize said case study, and wherein the display client is set up to map the pseudonymized case study, virtualized after transmission via an Internet connection, with the personal patient data and to display said case study on the viewer.

The expression "system" denotes an arrangement of computers, at least one of which is situated in a hospital environment and a further computer of which is situated in a computing center. In this case, hospital environment is used to mean that region (in physical terms or in terms of information technology) which is situated in the hospital or adjoins the hospital and is accessible only to the hospital staff or persons authorized for this purpose.

According to another embodiment of the system, the mapping is based on the use of the same marker which is used when generating the pseudonymized case study.

One embodiment of the invention provides a case upload client in a hospital environment, which client is set up to present medical contents, wherein a presentation client is set up in a computing center and a display client is set up in the hospital environment, wherein the presentation client can be used to virtualize contents and the display client can be used to display the virtualized contents by way of a viewer. The case upload client is set up to generate a pseudonymized case study from a patient study by providing the patient study with a marker and by removing personal patient data from the patient study. The case upload client is also set up to send the pseudonymized case study via a secure Internet protocol, and a case upload server in the computing center is set up to receive the pseudonymized case study via the secure Internet protocol and is equipped with an interface to a medical server in the computing center in order to forward the pseudonymized case study to the medical server. The presentation client is equipped with an interface to the medical server in order to retrieve the pseudonymized case study from the medical server and to virtualize said case study, and the display client is set up to map the pseudonymized case study, virtualized after transmission via an Internet connection, with the personal patient data and to display said case study on the viewer.

One embodiment of the invention provides a case upload server in a computing center, which server is set up to present medical contents, wherein a presentation client is set up in the computing center and a display client is set up in a hospital environment, wherein the presentation client can be used to virtualize contents and the display client can be used to display the virtualized contents by way of a viewer. A case upload client in the hospital environment is also set up to generate a pseudonymized case study from a patient study by providing the patient study with a marker and by removing personal patient data from the patient study and is also set up to send the pseudonymized case study via a secure Internet protocol. The case upload server is set up to receive the pseudonymized case study via the secure Internet protocol and is equipped with an interface to a medical server in the computing center in order to forward the pseudonymized case study to the medical server. The presentation client is equipped with an interface to the medical server in order to retrieve the pseudonymized case study from the medical server and to virtualize said case study, and the display client is set up to map the pseudonymized case study, virtualized after transmission via an Internet connection, with the personal patient data and to display said case study on the viewer.

One embodiment of the invention provides a storage medium for storing a computer program which can be read in and/or loaded by a digital computer and comprises instructions which are used to carry out the steps as claimed in the preceding method claims if the instructions are executed on the digital computer.

An alternative embodiment provides a storage medium which is intended to store the above-described, computer-implemented method and can be read by a computer.

Within the scope of the invention, not all steps of the method necessarily have to be carried out on the same computer entity but rather they can also be carried out on different computer entities. The sequence of method steps can also be varied, if necessary.

In addition, it is possible for individual sections of the above-described method to be carried out in one saleable unit and for the remaining components to be carried out in another saleable unit, as a distributed system so to speak.

Figure 1:
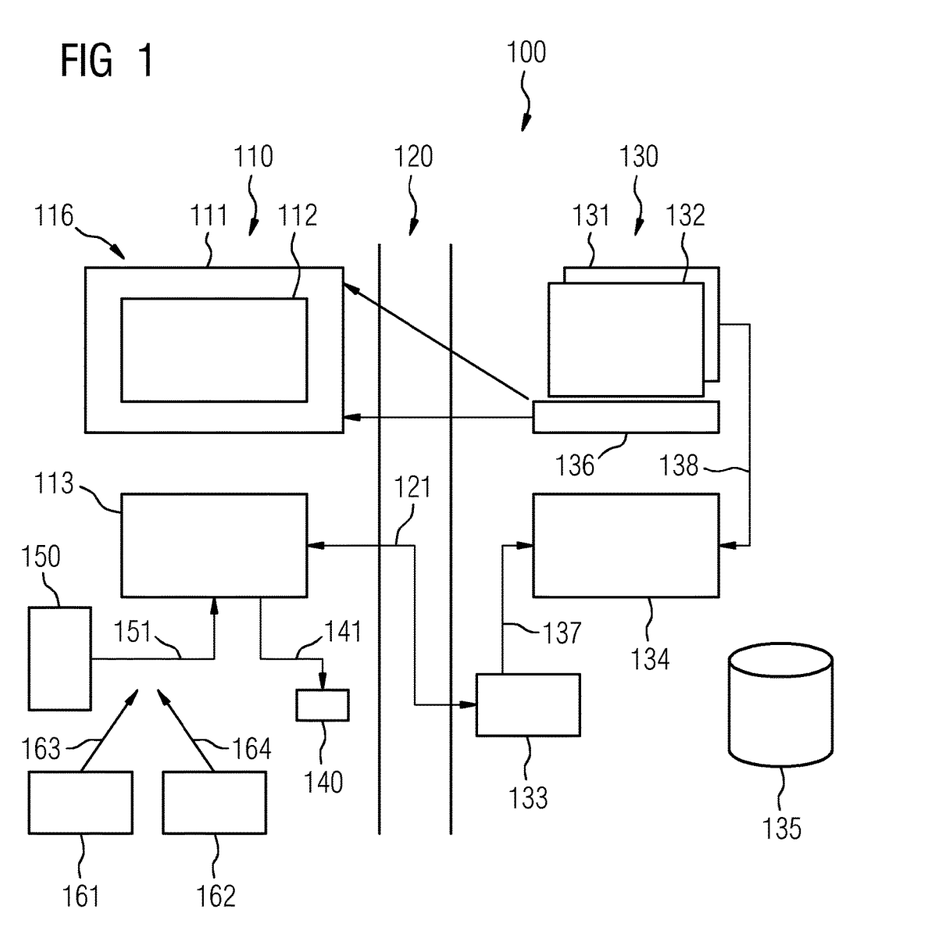
FIG. 1 shows an illustration of the system in the form of an overview in a first method stage.

FIG. 1 schematically shows the system 100 for presenting medical contents. The entire system 100 extends in a hospital environment 110, a computing center 130 and over the Internet 120. A display client 112 which, together with a viewer 111, is set up to present medical contents is situated in the hospital environment 110. The presentation can be effected in this case on a screen of a diagnostic workstation 116. Medical contents are formed by imaging medical devices which can also be referred to as an RIS station 161 and a PACS station 162 in accordance with their standards. In this case, the task of the system and of the method is to achieve RIS integration 163 and PACS integration 164. A case upload client 113 which is equipped with a connection according to the DICOM standard 151 by a medical provider 150 is provided for this purpose. The case upload client 113 is set up to pseudonymize image files stored according to the RIS or PACS standard. In this case, "pseudonymize" means that the data or image data are changed in such a manner that personal information relating to the patient is no longer present in the data. The case upload client 113 can then transmit the pseudonymized data. In particular, these data can be rendered anonymous 141 and can be passed to the pharmaceutical industry 140. The pseudonymized data, which are referred to as pseudonymized case studies below, can be first of all transmitted to a case upload server 133 via a secure Internet connection. In this case, transmission via a secure Internet protocol 121 hampers access to the transmitted pseudonymized case studies. Furthermore, the pseudonymized case studies do not have any indication of whom or which patients the data originate from. The case upload server 133 is set up to load the pseudonymized case studies and to transmit them 137 to a medical server 134. The medical server 134, together with a presentation client 132, is set up to present or virtualize 136 the pseudonymized case studies, in which case this presupposes loading 138 of the pseudonymized case studies into the presentation client 132.

Figure 2:
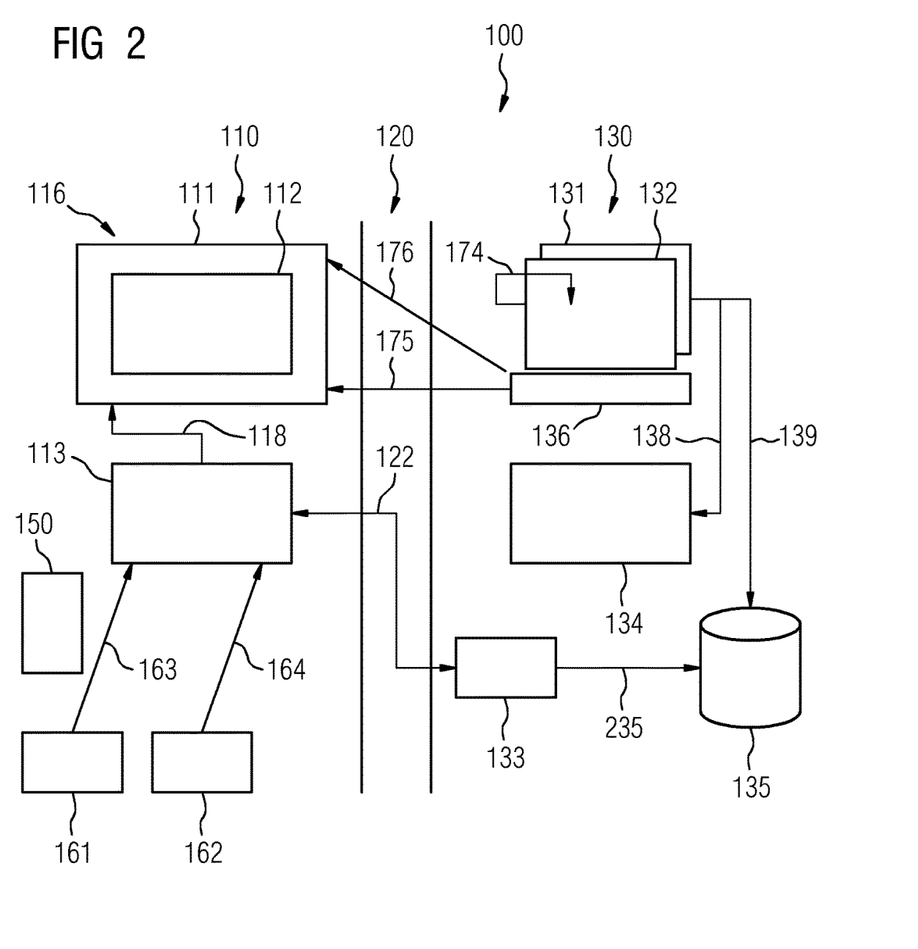
FIG. 2 shows an illustration of the system in the form of an overview in a second method stage.

FIG. 2 depicts the system for presenting medical contents in a second method stage. In this case, a user initiates, by way of the input on an input device of the diagnostic workstation 116, that a patient study is intended to be presented. If the RIS integration 163 or PACS integration 164 of the patient study has not yet taken place, the case upload client can retrieve the corresponding data and can transmit the latter via the secure Internet connection mentioned or a secure Internet protocol 121. A security feature 122 can be transmitted at the same time. However, the pseudonymized case studies may also have already been transmitted, with the result that a security feature 122 is transmitted later if the user would like to call up the patient study sometime for viewing or processing. The security feature is recorded on the case upload server 133 and is transmitted to a database 135. The transmission and storage of the identification feature 235 in the database 135 can be used to manage access rights for different users in different facilities or hospitals. Furthermore, the case upload client may induce a viewer start 116. The viewer start results in remote initialization 175 between the display client 112 and the presentation client 132. The identification feature is almost simultaneously retrieved from the presentation client 132 or a further presentation client 131 at the level of the computing center 130. After the identification feature has been requested 139 by the presentation client 132, the pseudonymized case study is presented via an Internet connection 176 in the event of authorization. The pseudonymized case study is mapped together with the personal patient data which were previously stored and remained in the hospital environment and is displayed on the viewer 111. In this case, a so-called "local call-up", that is to say an uploading of the pseudonymized case study in situ in the hospital, is finally carried out again, said case study being provided in a virtualized manner by the presentation client 132. The user at the diagnostic workstation 116 finally sees a complete patient study.

In conclusion, it is pointed out that the description of the invention and the example embodiments should fundamentally not be understood in a restrictive manner with respect to a particular physical implementation of the invention. In particular, it is obvious to a person skilled in the art that the invention can be partially or completely implemented in a distributed manner in software and/or hardware and/or on a plurality of physical products, in particular also computer program products in this case.

What is claimed is:

1. A method for presenting medical contents, the method comprising:
   generating, via a client associated with a hospital environment, a pseudonymized case study from a patient imaging study by replacing personal patient data from the patient imaging study with an anonymous marker exclusively maintained by the client, the anonymous marker being associated with the personal patient data;
   sending, via a secure Internet connection, the pseudonymized case study from the client to a server associated with a computing center;
   formulating, by the client, an identification feature based on the anonymous marker maintained by the client, the identification feature identifying the pseudonymized case study without providing sufficient information to map the pseudonymized case study with the personal patient data, if a user of the client requests retrieval of the pseudonymized case study from the server;
   sending, via the client, the identification feature associated with the pseudonymized case study and a client identification associated with the client to the server such that the server is unable to map the pseudonymized case study with the personal patient data based on the identification feature;
   virtualizing, by the server, the pseudonymized case study by (i) initiating a remote display session with the client based on the client identification, (ii) performing a remote image call-up to load the pseudonymized case study from a database into a virtual machine associated with the server based on the identification feature, and (iii) transmitting the virtualized pseudonymized case study to a viewer associated with the client via the remote display session;
   mapping, via the client, the virtualized pseudonymized case study with the personal patient data based on the anonymous marker exclusively maintained by the client to generate mapped medical contents; and
   displaying, on the viewer associated with the client, the mapped medical contents.

2. The method of claim 1, further comprising:
   storing, by the server, the identification feature in the database associated with the server.

3. A system for presenting medical contents, the system comprising:
   a server associated with a computing center; and
   a client associated with a hospital environment,
   wherein the client is configured to,
      generate a pseudonymized case study from a patient imaging study by replacing personal patient data from the patient imaging study with an anonymous marker exclusively maintained by the client, the anonymous marker being associated with the personal patient data, and
      send, via a secure Internet connection, the pseudonymized case study from the client to the server,
      formulate, by the client, an identification feature based on the anonymous marker maintained by the client, the identification feature identifying the pseudonymized case study without providing sufficient information to map the pseudonymized case study with the personal patient data, if a user of the client requests retrieval of the pseudonymized case study from the server;
      send, via the client, the identification feature associated with the pseudonymized case study and a client identification associated with the client to the server such that the server is unable to map the pseudonymized case study with the personal patient data based on the identification feature;
      map, via the client, virtualized pseudonymized case study with the personal patient data based on the anonymous marker exclusively maintained by the client to generate mapped medical contents, and
      display, on a viewer associated with the client, the mapped medical contents; and
   wherein server is configured to,
      virtualize the pseudonymized case study by (i) initiating a remote display session with the client based on the client identification, (ii) performing a remote image call-up to load the pseudonymized case study from a database into a virtual machine associated with the server based on the identification feature, and (iii) transmitting the virtualized pseudonymized case study to the viewer associated with the client via the remote display session.

4. A client associated with a hospital environment, the client comprising:
   a processor configured to,
      generate a pseudonymized case study from a patient imaging study by replacing personal patient data from the patient imaging study with an anonymous marker exclusively maintained by the client, the anonymous marker being associated with the personal patient data maintained by the client,
      send, via a secure Internet connection, the pseudonymized case study to a server associated with a computing center,
      formulate an identification feature based on the anonymous marker maintained by the client, the identification feature identifying the pseudonymized case study without providing sufficient information to map the pseudonymized case study with the personal patient data, if a user of the client requests retrieval of the pseudonymized case study from the server, send the identification feature associated with the pseudonymized case study and a client identification associated with the client to the server such that the server is unable to map the pseudonymized case study with the personal patient data based on the identification feature, receive a virtualized pseudonymized case study from the computing center by (i) accepting a remote display session with the computing center initiated based on the client identification, and (ii) receiving the virtualized pseudonymized case study by a viewer associated with the client via the remote display session such that the virtualized pseudonymized case study is run on a virtual machine associated with the server based on the identification feature, map the virtualized pseudonymized case study with the personal patient data based on the anonymous marker exclusively maintained by the client to generate mapped medical contents, and display, on the viewer associated with the client, the mapped medical contents.

5. The method of claim 1, wherein the displaying displays the mapped medical contents on a diagnostic workstation associated with the hospital environment.

6. A method for presenting medical contents, comprising:

generating, via a client associated with a hospital environment, a pseudonymized case study from a patient imaging study by replacing personal patient data from the patient imaging study with an anonymous marker maintained by the client, the anonymous marker being associated with the personal patient data exclusively maintained by the client;

sending, via a secure Internet connection, the pseudonymized case study from the client to a computing center to virtualize the pseudonymized case study;

formulating, by the client, an identification feature based on the anonymous marker maintained by the client, the identification feature identifying the pseudonymized case study without providing sufficient information to map the pseudonymized case study with the personal patient data, if a user of the client requests retrieval of the pseudonymized case study from the computing center;

sending, via the client, the identification feature associated with the pseudonymized case study and a client identification associated with the client to the computing center such that the computing center is unable to map the pseudonymized case study with the personal patient data based on the identification feature;

receiving the virtualized pseudonymized case study from the computing center by (i) accepting a remote display session with the computing center initiated based on the client identification, and (ii) receiving the virtualized pseudonymized case study by a viewer associated with the client via the remote display session such that the virtualized pseudonymized case study is run on a virtual machine associated with the computing center based on the identification feature;

mapping the virtualized pseudonymized case study with the personal patient data to generate mapped medical contents; and displaying, on the viewer associated with the client, the mapped medical contents.

* * * * *